United States Patent [19]

Ehrig et al.

[11] 4,220,779
[45] Sep. 2, 1980

[54] PROCESS FOR THE PREPARATION OF QUINOLINE DERIVATIVES

[75] Inventors: Volker Ehrig, Bergisch-Gladbach, Fed. Rep. of Germany; Hans-Samuel Bien, deceased, late of Burscheid, Fed. Rep. of Germany, by Else Bien, Gabriele Bien, Dorothee Bien, legal representatives; Erich Klauke, Odenthal; Detlef-Ingo Schütze, Bergisch-Gladbach, both of Fed. Rep. of Germany

[73] Assignee: Bayer Aktiengesellschaft, Leverkusen, Fed. Rep. of Germany

[21] Appl. No.: 920,778

[22] Filed: Jun. 30, 1978

[30] Foreign Application Priority Data

Jul. 2, 1977 [DE] Fed. Rep. of Germany ....... 2730061

[51] Int. Cl.² .................. C07D 215/12; C07D 215/14; C07D 215/18; C07D 215/54
[52] U.S. Cl. .................................. 546/152; 546/156; 546/176; 546/180; 546/153
[58] Field of Search ....... 260/287 G, 283 CN, 289 R, 260/283 SY; 546/152, 156, 176, 180

[56] References Cited

U.S. PATENT DOCUMENTS 3,907,808  9/1975  Lesher et al. ................. 260/287 AN
4,139,533  2/1979  Buchanan et al. .................. 546/156

OTHER PUBLICATIONS

March, "Advanced Organic Chemistry", (1968) pp. 303, 658.
Elderfield, "Heterocyclic Compounds", vol. 4, pp. 208-210 (1957).

Primary Examiner—Nicholas S. Rizzo
Assistant Examiner—David E. Wheeler
Attorney, Agent, or Firm—Sprung, Felfe, Horn, Lynch & Kramer

[57] ABSTRACT

Quinoline derivatives, especially those of the formula

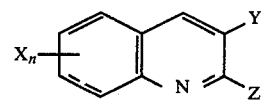

wherein
  X represents halogen, nitro or $CF_3$,
  Z represents hydrogen, alkyl or aryl,
  Y represents hydrogen, OH, CN, COR or $SO_3H$,
  R represents alkyl, alkoxy or aryl and
  n represents an integer from 0 to 4, are obtained in high yields when corresponding aromatic orthodichloromethyl isocyanates are converted by hydrolysis and decarboxylation into the corresponding ortho-aminoaldehydes and these are subjected to a condensation reaction with carbonyl compounds containing an active α-methylene group.

The process products are starting materials for dyestuffs, insecticides and others.

3 Claims, No Drawings

PROCESS FOR THE PREPARATION OF QUINOLINE DERIVATIVES

The subject of the invention is a new process for the preparation of quinolines, preferably 3-hydroxyquinolines.

Amongst the numerous known quinoline syntheses, the Friedländer method, in which aromatic o-aminocarbonyl compounds are subjected to an alkaline condensation reaction with carbonyl compounds containing an active methylene group, is one of the most commonly used, because of its universal applicability.

On the other hand, because the o-amino-benzaldehydes required for this reaction are not readily accessible and are of low stability, this synthesis principle has not been able to find acceptance industrially, but hitherto has a rule remained restricted to the laboratory scale (in this context compare "Heterocyclic Compounds" volume 4, page 46 by R. C. Elderfield).

It has now been found that quinolines are obtained in comparatively high yields and also on an industrial scale employing the Friedländer principle — at least in the broadst sense — when the relatively stable aromatic ortho-dichloro-methyl isocyanates, which can be handled easily, are converted by hydrolysis and decarboxylation into the corresponding ortho-aminoaldehydes and these are subjected to a condensation reaction with carbonyl compounds containing an active α-methylene group.

The new process is particularly suitable for the preparation of quinolines of the formula

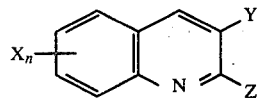

wherein
X represents hydrogen, nitro or CF$_3$,
Z represents hydrogen, alkyl or aryl,
Y represents hydrogen, OH, CN, COR or SO$_3$H,
R represents alkyl, alkoxy or aryl and
n represents an integer from 0 to 4 and
the alkyl, alkoxy and aryl radicals are optionally substituted and X and Y together can form an alkylene chain or the radical

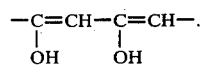

Suitable alkyl radical have 1–4 C atoms and can be substituted by halogen, CN, C$_1$-C$_4$-alkoxy and others. The methyl radical is preferred. Suitable aryl radicals are phenyl radicals, which can be substituted by halogen, NO$_2$, C$_1$-C$_4$-alkyl or C$_1$-C$_4$-alkoxy.

Suitable alkylene radicals have at least 3 C atoms, such as, for example, —(CH$_2$)—$_3$ and —(CH$_2$)—$_4$.

Within the scope of this invention, "halogen" is understood as meaning F, Br and, above all, Cl.

If X denotes a nitro group, n preferably represents the number 1.

Compounds preferably to be prepared correspond to the formula I given above, wherein
X represents chlorine,
Z represents C$_1$-C$_4$-alkyl, preferably methyl,
Y represents OH or —CO—C$_1$-C$_4$-alkyl, preferably acetyl; COOCH$_3$ or COOC$_2$H$_5$ and
n represents 0 to 4, preferably 0–2.

When carrying out the process according to the invention in practice, the procedure is appropriately that the dichloromethyl isocyanate is treated in an aqueous medium, which can contain, as a solubilising agent, an inert organic solvent and optionally an inert surface-active agent, with alkali, preferably an alkaline earth metal hydroxide, at temperatures of −5 to 50° C. and preferably 5 to 35° C., whilst stirring vigorously, until no further isocyanate can be detected (for example, by IR spectroscopy) in a sample (15–90 and preferably 30–45 minutes), subsequently—preferably after cooling to 0°–5° C. and adding an anti-foaming agent, the pH value is adjusted to 4–7 and preferably 5–6 by adding a mineral acid and, after the evolution of CO$_2$ has ceased, the reaction mixture is reacted (time 1–6 and preferably 2–4 hours) in a manner which is in itself known under alkaline conditions with a carbonyl compound containing an active αmethylene group to give the corresponding quinoline, which after neutralisation can be isolated in a conventional manner.

Suitable dichloromethyl isocyanates for carrying out the process according to the invention are those of the formula

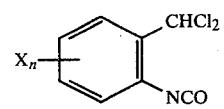

wherein X and n have the abovementioned meaning.

Examples which may be mentioned are: 2-dichloromethyl-phenyl isocyanate, 3-chloro-2-dichloromethyl-phenyl isocyanate, 4-chloro-2-dichloromethyl-phenyl isocyanate, 4-bromo-2-dichloromethyl-phenyl isocyanate, 5-chloro-2-dichloromethyl-phenyl isocyanate, 6-chloro-2-dichloromethyl-phenyl isocyanate, 4,6-dichloro-2-dichloromethyl-phenyl isocyanate, 3,4,6-trichloro-2-dichloromethyl-phenyl isocyanate, tetrachloro-2-dichloromethyl-phenyl isocyanate, 5-fluoro-2-dichloromethyl-phenyl isocyanate, 3,4-dichloro-2-dichloromethyl-phenyl isocyanate, 5-trifluoromethyl-2-dichloromethyl-phenyl isocyanate and 4-nitro-2-dichloromethyl-phenyl isocyanate.

Suitable organic solvents are chemically inert towards the isocyanate and have a good solvent power both in respect of the isocyanate and in respect of the carbonyl compound.

Examples which may be mentioned are: benzene, toluene, chlorobenzene, xylene and the like.

Suitable alkaline earth metal hydroxides are magnesium hydroxide, calcium hydroxide, stronthium hydroxide and, above all, barium hydroxide, which can be employed in solution or in dispersion.

The mineral acid used to adjust the pH value to 4–7 can be, above all, hydrochloric acid.

Suitable carbonyl compounds correspond to the formula

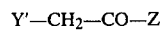

wherein
Y′ represents Y or halogen (preferably Cl and Br), halogen being converted to OH in the course of the condensation reaction, and Z has the abovementioned meaning.

Examples which may be mentioned are: acetaldehyde, acetone, chloroacetone and bromoacetone, δ-chloroacetophenone, cyclohexanone, phloroglucinol, acetylacetone, barbituric acid, cyanoacetone, acetonesulphonic acid, ethyl acetoacetate and others.

The reaction with these compounds to give the quinolines can be catalysed by the addition of customary alkalis (such as NaOH, KOH, $Na_2CO_3$, $Ca(OH)_2$ and others).

The vigorous thorough mixing of the reaction mixture, which is necessary in order to achieve optimum yields, can be effected, for example, with the aid of a baffle and of an impeller stirrer.

Before neutralising the reaction mixture at the end of the reaction, it is advisable to filter off undissolved alkaline earth metal hydroxides.

The alkaline earth metal chloride contained in the final mother liquor (if neutralised with HCl) can be recovered in the form of the sparingly soluble alkaline earth metal hydroxide by adding an alkali metal hydroxide.

The present invention also relates to new quinoline derivatives of the formula I, wherein
n represents 1 to 4 and preferably 2 to 4 and
Y represents CN or COR.

Preferred new quinoline derivatives are those of the formula I, wherein
X represents chlorine, bromine, $CF_3$ or $NO_2$,
Z represents H, methyl or phenyl,
Y represents acetyl, $COOCH_3$ or $COOC_2H_5$ and
n represents the numbers 1–4, preferably 2–4 when X=Cl or Br and represents the number 1 when X=$NO_2$ or $CF_3$.

Amongst these derivatives, those in which Y represents acetyl and Z represents methyl are preferred.

The new and known compounds of the formula I can be used in many ways.

For example, compounds of the indicated formula wherein Z represents methyl are starting materials for the synthesis of valuable quinophthalone dyestuffs.

Compounds of the formula I in which Y=OH are suitable as coupling components for the preparation of azo dyestuffs.

Moreover, these compounds can be converted by reaction with isocyanates or phosphoric said ester-chlorides to the corresponding carbamates, or, respectively, phosphoric acid esters, which possess insecticidal properties.

Some of the compounds of the formula I in which Y=acetyl are valuable analgesics.

EXAMPLE 1

48 g (0.24 mol) of 2-dichloro-methyl-phenyl isocyanate are allowed to run into a suspension of barium hydroxide (prepared by adding 80 g (1 mol) of 50% strength NaOH to a solution of 125 g (0.53 mol) of barium chloride) in 650 ml of water, at 15°–18° C., whilst stirring vigorously (with the aid of a baffle and an impeller stirrer). The mixture is stirred for a further 30–40 minutes at this temperature and about 100 ml of 10% strength hydrochloric acid are then added dropwise, at 3°–5° C., to the reaction mixture until the pH is 5–6, $CO_2$ being evolved. In order to prevent foaming over, it is advisable occasionally to add a few drops of a commercially available silicone defoaming agent. After the evolution of $CO_2$ has subsided, the reaction mixture is rendered alkaline with about 120 ml of 30% strength NaOH, whereupon the temperature rises to 8°–10° C. After removing the external cooling bath, 24.4 g (0.264 mol) of chloroacetone are then added and the mixture is stirred for a further 2–4 hours at room temperature. It is then filtered, the filter residue is washed with a little dilute NaOH and the pH of the filtrate is adjusted to 7 with about 130 ml of 20% strength HCl. The 3-hydroxyquinaldine which precipitates out is filtered off, washed with water and dried at 70°–90° C. Yield: 34.2 g (90%). The melting point is 259°–63° C.

If the procedure followed is as indicated above but the reaction is carried out under the conditions indicated in the Table which follows, corresponding quinoline derivatives are again obtained in approximately equally good yields:

Table 1

| Example | Isocyanate | Carbonyl compound | Base | Hydrolysis temperature (°C.) | End product | Melting point or decomposition point (°C.) |
| --- | --- | --- | --- | --- | --- | --- |
| 2 | 2-Dichloromethyl-phenyl isocyanate | Acetaldehyde | $Ba(OH)_2$ | 8–10 | Quinoline | boiling point 234–6 |
| 3 | 2-Dichloromethyl-phenyl isocyanate | Acetone | $Ba(OH)_2$ | 5–8 | Quinaldine | boiling point 243–7 |
| 4 | 2-Dichloromethyl-phenyl isocyanate | Chloroacetaldehyde | $Sr(OH)_2$ | 12–15 | 3-Hydroxyquinoline | 194–97 |
| 5 | 2-Dichloromethyl phenyl isocyanate | Chloroacetone | $Ca(OH)_2$ | 5–8 | 3-Hydroxyquinaldine | 259–63 |
| 6 | 2-Dichloromethyl-phenyl isocyanate | Chloroacetone | KOH | 3–5 | 3-Hydroxyquinaldine | 259–63 |
| 7 | 2-Dichloromethyl-phenyl isocyanate | Acetonesulphonic acid | $Ba(OH)_2$ | 5–8 | Quinaldine-3-sulphonic acid | 270 |

If the procedure followed is as in Example 1 but the starting materials indicated below are employed, the following quinoline derivatives are obtained.

Table 2

| Ex. | Isocyanate | Carbonyl compound | End product | Melting point or decomposition point (°C.) |
| --- | --- | --- | --- | --- |
| 8 | 3-Chloro-2-dichloromethyl-phenyl isocyanate | Chloroacetone | 5-Chloro-3-hydroxyquinaldine | 240 |
| 9 | 4-Chloro-2-dichloromethyl-phenyl isocyanate | Chloroacetone | 6-Chloro-3-hydroxyquinaldine | 270–75 |
| 10 | 5-Chloro-2-dichloro- | Chloro- | 7-Chloro-3- | 268–72 |

Table 2-continued

| Ex. | Isocyanate | Carbonyl compound | End product | Melting point or decomposition point (°C.) |
|---|---|---|---|---|
|  | methyl-phenyl isocyanate | acetone | hydroxyquinaldine |  |
| 11 | 6-Chloro-2-dichloromethyl-phenyl isocyanate | Chloroacetone | 8-Chloro-3-hydroxyquinaldine | 203–4 |
| 12 | 5-Fluoro-2-dichloromethyl-phenyl isocyanate | Chloroacetone | 7-Fluoro-3-hydroxyquinaldine | 242–48 |
| 13 | 5-Trifluoromethyl-2-dichloromethyl-phenyl isocyanate | Chloroacetone | 7-Trifluoromethyl-3-hydroxyquinaldine | 250–56 |
| 14 | 3,4-Dichloro-2-dichloromethyl-phenyl isocyanate | Chloroacetone | 5,6-Dichloro-3-hydroxyquinaldine | 290–315 |
| 15 | 3,6-Dichloro-2-dichloromethyl-phenyl isocyanate | Chloroacetone | 5,8-Dichloro-3-hydroxyquinaldine | 280–95 |
| 16 | 3,4,6-Trichloro-2-dichloro-methyl-phenyl isocyanate | Chloroacetone | 5,6,8-Trichloro-3-hyquinaldine | 305–15 |

EXAMPLE 17

60 g (0.19 mol) of $Ba(OH)_2 \times 8H_2O$ and 14.3 g (0.042 mol) of tetrachloro-2-dichloromethyl-phenyl isocyanate are mixed well and the mixture is introduced into 450 ml of water with the addition of 1 ml of toluene. The mixture is stirred for 6–8 hours at 20°–25° C. whilst stirring vigorously (with the aid of a baffle and an impeller stirrer) and the pH value is then adjusted to 2–3 with the addition of 89 ml of 10% strength hydrochloric acid at 0°–5° C. After the evolution of $CO_2$ has ceased, 30 ml of concentrated NaOH are added dropwise, whereupon the temperature rises to 12° C. 6.5 g (0.07 mol) of chloroacetone are then allowed to run in dropwise in the course of 15 minutes, the temperature being slowly raised to 50° C. After stirring for 3 hours at 50° C., the pH of the reaction mixture is adjusted to 2, at 20°–25° C., with 75 ml of 20% strength hydrochloric acid and the residue is filtered off, washed and dried. Recrystallisation from 0-dichlorobenzene results in 5,6,7,8-tetrachloro-3-hydroxyquinaldine with a decomposition point of 270° C. The yield of 10.5 g is 85% of theory.

EXAMPLE 18

38.4 g (0.19 mol) of 2-dichloromethyl-phenyl isocyanate are allowed to run into a suspension of 135 g (0.43 mol) of $Ba(OH)_2 \times 8H_2O$ in 500 ml of water, at 15°–18° C. whilst stirring vigorously (with the aid of a baffle and an impeller stirrer). The mixture is stirred for a further 30–40 minutes at this temperature and about 95 ml of 10% strength hydrochloric acid are added dropwise to the reaction mixture, at 3°–5° C., until the pH is 5–6, $CO_2$ being evolved. After the evolution of $CO_2$ has subsided, the reaction mixture is rendered alkaline with 4 ml of 50% strength NaOH. After removing the external cooling bath, 25 g (0.25 mol) of acetylacetone are then allowed to run in dropwise in the course of 15–30 minutes and the mixture is stirred for a further 4–6 hours at room temperature. It is then filtered and the filter residue is taken up in methanol and warmed to 40° C.

After cooling, the undissolved barium salt is filtered off and the filtrate is evaporated. After drying in a desiccator, 33 g (94% of theory) of 3-acetyl-3-hydroxy-quinaldine with a melting point of 54°–56° C. are obtained.

If the procedure followed is as in Example 18 but the starting materials indicated below are employed, the following quinoline derivatives are obtained:

Table 3

| Example | Isocyanate | Carbonyl compound | End product | Melting point or decomposition point (°C.) |
|---|---|---|---|---|
| 19 | 2-Dichloromethyl-phenyl isocyanate | Cyclohexanone | 1,2,3,4-Tetrahydroacridine | 52 |
| 20 | 2-Dichloromethyl-phenyl isocyanate | Ethyl acetoacetate | Ethyl 2-methyl-quinoline-3-carboxylate | 70–72 |
| 21 | 2-Dichloromethyl-phenyl isocyanate | Methyl acetoacetate | Methyl 2-methyl-quinoline-3-carboxylate | 69–71 |

We claim:

1. A process for the prepartion of quinoline wherein an aromatic ortho-dichloromethyl isocyanate of the formula

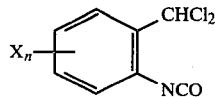

wherein
X represents halogen, nitro or $CF_3$ and
n represents an integer from 0 to 4 with the value being 1 when X is nitro or $CF_3$ and being 1–4 when X is halogen; is treated with barium hydroxide to produce the corresponding ortho-aminoaldehyde, which is then reacted, without isolation from the reaction medium, with a carbonyl compound containing an active α-methylene group and having the formula

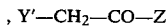

wherein
Y' represents H, OH, CN, COR, halogen, or $SO_3H$;
Z represents H, $C_1$–$C_4$, alkyl, phenyl, halophenyl, nitrophenyl, $C_1$–$C_4$-alkylphenyl or $C_1$–$C_4$-alkoxyphenyl and
R represents $C_1$–$C_4$ alkyl, $C_1$–$C_4$ alkoxy, or phenyl; $C_1$–$C_4$ haloalkyl, $C_1$–$C_4$ cyanoalkyl, $C_1$–$C_4$-alkoxyalkyl, halophenyl, nitrophenyl, $C_1$–$C_4$-alkylphenyl or $C_1$–$C_4$-alkoxyphenyl; and
Z and Y', when joined together, are $C_2$–$C_4$ are alkylene or

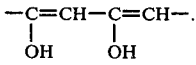

2. Quinolines of the formula

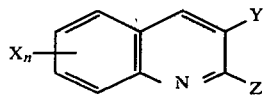

wherein
- X is halogen, nitro, or $CF_3$;
- Z is hydrogen, $C_1$–$C_4$-alkyl, halo-$C_1$–$C_4$-alkyl, cyano-$C_1$–$C_4$-alkyl, $C_1$–$C_4$-alkoxy-$C_1$–$C_4$-alkyl, phenyl, halophenyl, nitrophenyl, $C_1$–$C_4$-alkylphenyl, or $C_1$–$C_4$-alkoxyphenyl;
- Y is CN or COR;
- R is $C_1$–$C_4$-alkyl, $C_1$–$C_4$-alkoxy, phenyl, halo-$C_1$–$C_4$-alkyl, cyano-$C_1$–$C_4$-alkyl, $C_1$–$C_4$-alkoxy-$C_1$–$C_4$-alkyl, halophenyl, nitrophenyl, $C_1$–$C_4$-alkylphenyl, or $C_1$–$C_4$-alkoxyphenyl;

Z and Y, when joined together, are $C_3$–$C_4$-alkylene or

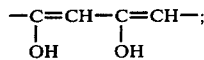

and
- n is an integer from 0 to 4, with the value being 1 when X is nitro or $CF_3$ and being 1–4 when X is halogen.

3. Quinoline of claim 2 wherein
- X is chloro, bromo, $CF_3$, or $NO_2$;
- Z is H, methyl, or phenyl;
- Y is $COCH_3$, $COOCH_3$, or $COOC_2H_5$, and
- n is an integer from 1–4, with the value being 1 when x is $CF_3$ or $NO_2$ and being 2–4 when x is chloro or bromo.

* * * * *